United States Patent [19]

Kachhy

[11] Patent Number: 4,650,880

[45] Date of Patent: Mar. 17, 1987

[54] PURIFICATION OF SUBSTITUTED PHTHALIC ANHYDRIDES

[75] Inventor: Avinash Kachhy, Edison, N.J.

[73] Assignee: Stauffer Chemical Company, Westport, Conn.

[21] Appl. No.: 811,215

[22] Filed: Dec. 20, 1985

[51] Int. Cl.$^4$ .......................................... C07D 307/89
[52] U.S. Cl. ................................. 549/240; 549/243; 549/245; 549/246
[58] Field of Search ................ 549/240, 243, 245, 246

[56] References Cited

U.S. PATENT DOCUMENTS 2,671,054  3/1954  Bump et al. .................... 549/251 X Primary Examiner—Richard L. Raymond
Attorney, Agent, or Firm—Hensley M. Flash

[57] ABSTRACT

A process for purifying crude substituted phthalic anhydrides, e.g. 4-methylphthalic anhydride, derived from the dehydrogenation in the presence of bromine of a Diels-Alder addition product of a conjugated diene, e.g. isoprene, and maleic anhydride. In this process, a mixture of the crude, liquid substituted phthalic anhydride, e.g. 4-methylphthalic anhydride, and an alkali is heated to a temperature effective to reduce the impurities present in the crude substituted phthalic anhydride. Suitable alkalis can include sodium hydroxide and sodium carbonate. Mild alkalis are heated to a higher temperature, e.g. 130° C. for sodium carbonate, whereas stronger alkalis are heated to a lower temperature, e.g. 90° C. for sodium hydroxide.

6 Claims, No Drawings

PURIFICATION OF SUBSTITUTED PHTHALIC ANHYDRIDES

BACKGROUND OF THE INVENTION

1. Field of the Invention

This invention relates to a process for purifying substituted phthalic anhydrides. More particularly, it relates to a process for purifying 4-methylphthalic anhydride derived from the dehydrogenation in the presence of bromine of 4-methyl-1,2,3,6-tetrahydrophthalic anhydride.

2. Related Art

Phthalic anhydrides are valuable raw materials for making various useful products. These anhydrides are useful as intermediates in the chemical synthesis of herbicides, and particularly in the synthesis of certain herbicides used to protect cereal crops. Other uses for these raw materials include polycyclic dyes, alkyd and epoxy resins, polyesters and plasticizers.

Various processes are known for preparing these substituted phthalic anhydrides. In many of these processes, a Diels-Alder addition product of a conjugated diene and maleic anhydride is dehydrogenated in the presence of bromine. The use of bromine in this dehydrogenation step introduces many impurities including hydrobromic acid and various brominated compounds. An effective economic means of purifying these substituted phthalic anhydrides, especially by reducing the hydrobromic acid and other brominated impurities, would be advantageous because the various useful products that are prepared from these anhydrides can be adversely affected by the presence of these impurities.

Chemical Abstract 84:105240Or, *Purification of Phthalic Anhydride* discloses the distillative purification of phthalic anhydride in the presence of zinc-containing materials as catalysts.

Chemical Abstract 70:77612d, *Phthalic Anhydride Purification from Hydrobromic Acid* discloses the purification of crude phthalic anhydride by heating at above 500° F. with passage through a fractionating stripper column in countercurrent flow.

SUMMARY OF THE INVENTION

A process for purifying crude substituted phthalic anhydrides in a more economic manner than heretofore known would be advantageous. It is an object of the present invention to provide a unique, cost-effective process for the purification of crude substituted phthalic anhydrides. Other objects and advantages of the present invention are shown throughout the specification.

In accordance with the present invention, it has now been discovered that crude substituted phthalic anhydride derived from the dehydrogenation in the presence of bromine of a Diels-Alder addition product of a conjugated diene and maleic anhydride can be purified by a process comprising heating a mixture of the crude, liquid substituted phthalic anhydride and an alkali to a temperature effective to reduce impurities.

DETAILED DESCRIPTION OF THE INVENTION

In the purification process of this invention, the crude substituted phthalic anhydride is derived from a Diels-Alder addition product. The Diels-Alder addition product is formed by reacting maleic anhydride with a conjugated diene. The conjugated diene can include butadiene, 2,3-dimethylbutadiene, other substituted butadienes and preferably isoprene. The term "substituted phthalic anhydride" is used throughout this application to include the compound phthalic anhydride which is formed by reacting maleic anhydride with the conjugated diene, butadiene, then dehydrogenating the resulting Diels-Alder addition product in the presence of bromine.

This addition product can be prepared by reacting the maleic anhydride with the conjugated diene in a nitrogen atmosphere. The maleic anhydride is usually heated until it melts, then the conjugated diene is added slowly under the surface of the melt. When the addition of the diene is completed, the reactants can then be heated to a reaction temperature of from about 55° C. up to about 120° C. with temperatures in the upper end of the range from about 100° C. up to about 120° C. being preferred. The reactants are kept within the reaction temperature range until the reaction is completed, usually for about 1 hour. The reaction can be exothermic, therefore external cooling may be required to maintain the reactants within the reaction temperature range.

The reaction to form the Diels-Alder addition product can take place in the presence or absence of an appropriate solvent. Usually when a solvent is used, a solution of the addition product in the solvent results and no solids are formed during the reaction. After the reaction to form the addition product is completed, excess diene can be stripped from the reaction zone under vacuum at a pressure which minimizes sublimation of the addition product or distillation of the solvent.

The stoichiometry of this Diels-Alder addition reaction usually involves 1 mole of the maleic anhydride reacting with 1 mole of the conjugated diene to produce 1 mole of the addition product. Therefore, it is economically desirable to react equimolar quantities of the reactants. However, a fractional molar excess of the diene, is usually used to ensure that all the maleic anhydride is consumed in the reaction.

This Diels-Alder addition product can then be dehydrogenated in the presence of bromine to yield the crude substituted phthalic anhydride. In a typical preparation, the Diels-Alder addition product can either be dissolved in a suitable solvent or heated to form a melt, then the solution or melt is treated with bromine.

A typical process for preparing the crude substituted phthalic anhydride, which is purified by the process of this invention, is disclosed in the allowed U.S. patent application Ser. No. 600,247 filed Apr. 16, 1984 by J. E. Telschow, now U.S. Pat. No. 4,560,773, in which the Diels-Alder addition product of a conjugated diene and maleic anhydride is reacted with bromine in the presence of a catalytic quantity of an acid acceptor, e.g. dimethylformamide and pyridene. Another such process is disclosed in the allowed U.S. patent application Ser. No. 600,248 filed Apr. 16, 1984 by J. E. Telschow, now U.S. Pat. No. 4,559,405 in which the Diels-Alder addition product of a conjugated diene and maleic anhydride is reacted with bromine in the presence of an acid acceptor.

The sources of the crude substituted phthalic anhydride disclosed above are preferred sources. However, it is expected that other processes using bromine in the dehydrogenation of a Diels-Alder addition product of a conjugated diene and maleic anhydride can yield many of the impurities that are capable of being purified by the process of this invention.

In a preferred embodiment of this invention, 4-methylphthalic anhydride, (4-MPA), is purified. This 4-MPA can be prepared by reacting isoprene and maleic anhydride to form the Diels-Alder addition product, 4-methyl-1,2,3,6-tetrahydrophthalic anhydride, (4-MTPA), followed by the dehydrogenation of the 4-MTPA with bromine.

In the process of this invention, the crude substituted phthalic anhydride is dissolved in a solvent or heated to a liquid melt then mixed with an alkali. The resulting mixture is then heated to a temperature effective to reduce impurities. Suitable alkalis can include the hydroxide, bicarbonates and carbonates of ammonium alkali and alkaline earth elements with sodium hydroxide and sodium carbonate being preferred alkalis. The ideal amount of alkali is the calculated stoichiometric amount equivalent to the weight percent of hydrolyzable bromide present in the crude substituted phthalic anhydride. The amount of hydrolyzable bromide present in the crude substituted phthalic anhydride typically ranges from about 5 to about 10 weight percent.

The temperature to which the mixture of the liquid crude substituted phthalic anhydride and alkali is heated to reduce the impurities can range from about 90° C. to about 160° C. Specific temperatures within the above range can be chosen for optimum results based on the strength of the alkali being used in the mixture. Mild alkalis are preferably heated to a higher temperature whereas stronger alkalis are preferably heated to a lower temperature.

In a preferred embodiment of this process, crude liquid 4-MPA is mixed with sodium hydroxide then the resulting mixture is heated to at least 90° C. In another preferred embodiment of this invention, crude liquid 4-MPA is mixed with sodium carbonate then the mixture is heated to at least 130° C.

When the crude liquid substituted phthalic anhydride is mixed with the alkali, an exothermic reaction occurs. The reaction mixture can typically be stirred for about 1 hour at the reaction temperature to allow the purification process to proceed, then the treated crude substituted phthalic anhydride can be distilled in the usual way. The resulting distilled product can exhibit a better color than the untreated product and the purity of this resulting product can be several weight percent higher, e.g. from about 1 to about 5 weight percent. Hydrolyzable bromide impurities can be reduced from about a few weight percent to a tenth of a weight percent or less. The resulting purified substituted phthalic anhydride can also exhibit greater thermal stability during storage as judged by the color of the product.

The following experiments describe various embodiments of the invention. Other embodiments will be apparent to one of ordinary skill in the art from a consideration of this specification or practice of the invention disclosed herein. It is intended that the specifications and experiments be considered as exemplary only, with the true scope and spirit of the invention being indicated by the claims which follow the experiments.

EXPERIMENT 1

Four hundred grams of crude 4-methylphthalic anhydride containing 7.4 weight percent hydrolyzable bromine was placed in a three-neck, round-bottom flask fitted with a thermometer, stirrer and vent then melted and heated to 145° C. 18.5 grams of sodium carbonate anhydrous was added to the flask. This is the calculated stoichiometric amount equivalent to about 7 weight percent hydrolyzable bromide. The sodium carbonate was added with stirring and the temperature rose to 155° C. due to the exotherm of the reaction. The mixture was stirred for 1 hour at 140° C. The stirrer and vent were then removed and a Claisen head with air condenser was attached. The treated crude 4-methylphthalic anhydride was distilled at 165°–180° C. pot temperature and 158°–162° C. vapor temperature at 10 millimeters of pressure. 299 grams of distilled 4-methylphthalic anhydride was obtained.

Yield from crude 4-MPA: 74.7 weight percent
GC area of 4-MPA: 98.69 percent
GC area of 4-bromomethylphthalic anhydride: 0.14 percent The following results were obtained in a comparative experiment following the procedure above without the addition of sodium carbonate.

Yield of 4-MPA from crude 4-MPA: 80.2 weight percent
GC area of 4-MPA: 96.7 percent
GC area of 4-bromomethylphthalic anhydride: 1.17 percent

EXPERIMENT 2

Two hundred grams of crude 4-methylphthalic anhydride was melted in a three-neck, round-bottom flask by heating to 95° C. 7.5 grams of a 50 weight percent sodium hydroxide solution was added to the flask while stirring then the mixture was further stirred at 90° C. for 30 minutes. The flask was fitted with a Claisen head and air condenser and the treated 4-MPA was distilled at 158° C. pot temperature and 155° C. vapor temperature at 8 millimeters of pressure. A comparative experiment was run without the sodium hydroxide treatment. The purities of the resulting products are compared below.

|  | HPLC Purity % | Diacid Content Wt. % | Hydrolyzable Bromide Wt. % |
| --- | --- | --- | --- |
| Without alkali | 91.66 | 0.12 | 1.18 |
| With alkali | 96.18 | 0.12 | 0.16 |

What is claimed is:
1. A process for purifying a crude substituted phthalic anhydride derived from the dehydrogenation in the presence of bromine of a Diels-Alder addition product of a conjugated diene and maleic anhydride comprising heating a mixture of the crude, liquid substituted phthalic anhydride and an alkali to a temperature effective to reduce impurities, said temperature ranging from about 90° C. to about 160° C.
2. The process of claim 1 wherein said conjugated diene is isoprene.
3. The process of claim 1 wherein the alkali is sodium hydroxide and the mixture is heated to at least 90° C.
4. The process of claim 1 wherein the alkali is sodium carbonate and the mixture is heated to at least 130° C.
5. The process of claim 2 wherein the alkali is sodium hydroxide and the mixture is heated to at least 90° C.
6. The process of claim 2 wherein the alkali is sodium carbonate and the mixture is heated to at least 130° C.

* * * * *